United States Patent [19]

Aggarwal et al.

[11] Patent Number: 5,837,817
[45] Date of Patent: Nov. 17, 1998

[54] TUMOR NECROSIS FACTOR RECEPTOR-II-ASSOCIATED PROTEIN KINASE AND METHODS FOR ITS USE

[75] Inventors: Bharat B. Aggarwal; Bryant G. Darnay, both of Houston, Tex.

[73] Assignee: Research Development Foundation, Carson City, Nev.

[21] Appl. No.: 588,604

[22] Filed: Jan. 18, 1996

Related U.S. Application Data

[63] Continuation-in-part of Ser. No. 272,005, Jul. 7, 1994, abandoned.
[51] Int. Cl.⁶ .................................................. C07K 14/705
[52] U.S. Cl. .......................... 530/350; 530/351; 435/194
[58] Field of Search .......................... 435/194; 530/350, 530/351

[56] References Cited

U.S. PATENT DOCUMENTS 5,563,039  10/1996  Goeddel et al .......................... 435/69.1

OTHER PUBLICATIONS

Rubin et al, *Cancer Res* 52, 1992, pp. 878–882.
Darnay et al, *JBC* 269, 1994, p. 20299.
Darnay et al *JBC* 269, 1994, p. 19687.
Song et al, *Biochem J*. 309, 1995, p. 825.
Ching et al *Science* 267, 1995 p. 1494.
Gaiddel et al *J. Cell. Biochem*, 18a, 1994, p. 5, (#1101).
Mosialas et al. *Cell* 80, p. 389, 1995.
Rothe et al. *Cell* 78, 1994, p. 681.
Tartaglia et al *Cell* 74, 1993, p. 845.
Song et al *JBC* 269, 1994, p. 22492.
Sato et al *FEBS* 358, 1995, p. 113.
Zhang et al J Immunol 153, 1994, p. 3749.

*Primary Examiner*—Garnette D. Draper
*Attorney, Agent, or Firm*—Benjamin Aaron Adler

[57] ABSTRACT

The present invention provides an isolated and purified protein that associates with the cytoplasmic domain of the p80 form of the tumor necrosis factor receptor, having a molecular weight of 59 kDa on SDS-PAGE, is a phosphoprotein, and does not bind to the p60 form of the tumor necrosis factor receptor. Also provided is an isolated and purified protein kinase that associates with the cytoplasmic domain of the p80 form of the tumor necrosis factor receptor, said kinase phosphorylates both the p80 and p60 forms of the tumor necrosis factor receptor and phosphorylates a 59 kDa molecular weight protein associated with the cytoplasmic domain of the p80 form of the tumor necrosis factor receptor. Also provided are various methods of reducing the biological effects of tumor necrosis factor.

1 Claim, 17 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 32
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( x i ) SEQUENCE DESCRIPTION: SEQ ID NO:1:

CTAAGAGAAT TCGCTACCAA CGGTGGAAGT CC 32

( 2 ) INFORMATION FOR SEQ ID NO:2:

( i ) SEQUENCE CHARACTERISTICS:
        ( A ) LENGTH: 27
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( x i ) SEQUENCE DESCRIPTION: SEQ ID NO:2:

GACGTACTCG AGTCATCTGA GAAGACT 27

( 2 ) INFORMATION FOR SEQ ID NO:3:

( i ) SEQUENCE CHARACTERISTICS:
        ( A ) LENGTH: 33
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( i x ) FEATURE:

( x i ) SEQUENCE DESCRIPTION: SEQ ID NO:3:

CTAAGAGGAT    CCAAAAAGAA    GCCCTTGTGC    CTG                          3 3

( 2 ) INFORMATION FOR SEQ ID NO:4:

( i ) SEQUENCE CHARACTERISTICS:
        ( A ) LENGTH: 27
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( i x ) FEATURE:

( x i ) SEQUENCE DESCRIPTION: SEQ ID NO:4:

GACGTACTCG    AGTCATCTGA    GAAGACT                                2 7

( 2 ) INFORMATION FOR SEQ ID NO:5:

( i ) SEQUENCE CHARACTERISTICS:
        ( A ) LENGTH: 33
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:

(F) TISSUE TYPE:
                (G) CELL TYPE:
                (H) CELL LINE:

(ix) FEATURE:

(xi) SEQUENCE DESCRIPTION: SEQ ID NO:5:

CTAAGAGGAT   CCAAAAAGAA   GCCCTTGTGC   CTG                                             3

(2) INFORMATION FOR SEQ ID NO:6:

(i) SEQUENCE CHARACTERISTICS:
                (A) LENGTH: 33
                (B) TYPE: nucleic acid
                (C) STRANDEDNESS: double
                (D) TOPOLOGY: linear (ii) MOLECULE TYPE:
                (A) DESCRIPTION: other nucleic acid (iii) HYPOTHETICAL: No (iv) ANTI-SENSE: No (vi) ORIGINAL SOURCE:
                (B) STRAIN:
                (C) INDIVIDUAL ISOLATE:
                (D) DEVELOPMENTAL STAGE:
                (F) TISSUE TYPE:
                (G) CELL TYPE:
                (H) CELL LINE:

(ix) FEATURE:

(xi) SEQUENCE DESCRIPTION: SEQ ID NO:6:

CTAAGAGGAT   CCGGGACCCA   GGTCAATGTC   ACC                                             33

(2) INFORMATION FOR SEQ ID NO:7:

(i) SEQUENCE CHARACTERISTICS:
                (A) LENGTH: 33
                (B) TYPE: nucleic acid
                (C) STRANDEDNESS: double
                (D) TOPOLOGY: linear (ii) MOLECULE TYPE:
                (A) DESCRIPTION: other nucleic acid (iii) HYPOTHETICAL: No (iv) ANTI-SENSE: No (vi) ORIGINAL SOURCE:
                (B) STRAIN:
                (C) INDIVIDUAL ISOLATE:
                (D) DEVELOPMENTAL STAGE:
                (F) TISSUE TYPE:
                (G) CELL TYPE:
                (H) CELL LINE:

(ix) FEATURE:

(xi) SEQUENCE DESCRIPTION: SEQ ID NO:7:

CTAAGAGGAT   CCCAGCACCT   GCTGATCACA   GCG                                             33

(2) INFORMATION FOR SEQ ID NO:8:

(i) SEQUENCE CHARACTERISTICS:
                (A) LENGTH: 33
                (B) TYPE: nucleic acid
                (C) STRANDEDNESS: double
                (D) TOPOLOGY: linear (ii) MOLECULE TYPE:

( A ) DESCRIPTION: other nucleic acid ( i i i ) HYPOTHETICAL: No ( i v ) ANTI-SENSE: No ( v i ) ORIGINAL SOURCE:
           ( B ) STRAIN:
           ( C ) INDIVIDUAL ISOLATE:
           ( D ) DEVELOPMENTAL STAGE:
           ( F ) TISSUE TYPE:
           ( G ) CELL TYPE:
           ( H ) CELL LINE:

( i x ) FEATURE:

( x i ) SEQUENCE DESCRIPTION: SEQ ID NO:8:

CTAAGAGGAT    CCACAATGGG    AGACACAGAT    TCC                                     33

( 2 ) INFORMATION FOR SEQ ID NO:9:

( i ) SEQUENCE CHARACTERISTICS:
           ( A ) LENGTH: 34
           ( B ) TYPE: nucleic acid
           ( C ) STRANDEDNESS: double
           ( D ) TOPOLOGY: linear ( i i ) MOLECULE TYPE:
           ( A ) DESCRIPTION: other nucleic acid ( i i i ) HYPOTHETICAL: No ( i v ) ANTI-SENSE: No ( v i ) ORIGINAL SOURCE:
           ( B ) STRAIN:
           ( C ) INDIVIDUAL ISOLATE:
           ( D ) DEVELOPMENTAL STAGE:
           ( F ) TISSUE TYPE:
           ( G ) CELL TYPE:
           ( H ) CELL LINE:

( i x ) FEATURE:

( x i ) SEQUENCE DESCRIPTION: SEQ ID NO:9:

TCTTAGAAGC    TTTTAACTTG    GGCTTCATCC    CAGC                                    34

( 2 ) INFORMATION FOR SEQ ID NO:10:

( i ) SEQUENCE CHARACTERISTICS:
           ( A ) LENGTH: 33
           ( B ) TYPE: nucleic acid
           ( C ) STRANDEDNESS: double
           ( D ) TOPOLOGY: linear ( i i ) MOLECULE TYPE:
           ( A ) DESCRIPTION: other nucleic acid ( i i i ) HYPOTHETICAL: No ( i v ) ANTI-SENSE: No ( v i ) ORIGINAL SOURCE:
           ( B ) STRAIN:
           ( C ) INDIVIDUAL ISOLATE:
           ( D ) DEVELOPMENTAL STAGE:
           ( F ) TISSUE TYPE:
           ( G ) CELL TYPE:
           ( H ) CELL LINE:

( i x ) FEATURE:

( x i ) SEQUENCE DESCRIPTION: SEQ ID NO:10:

TCTTAGAAGC    TTTTAATGGC    CACCAGGGGA    AGA                                     33

( 2 ) INFORMATION FOR SEQ ID NO:11:

( i ) SEQUENCE CHARACTERISTICS:
        ( A ) LENGTH: 34
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( i x ) FEATURE:

( x i ) SEQUENCE DESCRIPTION: SEQ ID NO:11:

TCTTAGAAGC    TTTTACTCGT    CCTTCGGGGA    ACTC    34

TUMOR NECROSIS FACTOR RECEPTOR-II-ASSOCIATED PROTEIN KINASE AND METHODS FOR ITS USE

CROSS-REFERENCED TO RELATED APPLICATIONS

This application is a continuation-in-part of U.S. Ser. No. 08/272,005 filed Jul. 7, 1994, now abandoned.

BACKGROUND OF THE INVENTION

1. Field of the Invention

The present invention relates generally to the fields of cytokine physiology and protein chemistry. More specifically, the present invention relates to a novel serine-threonine protein kinase associated with the p80 form of the tumor necrosis factor receptor and various methods involving manipulating this protein kinase.

2. Description of the Related Art

Tumor necrosis factor (TNF), a homotrimer of 17 kDa subunits, is a cytokine produced mainly by activated macrophages and several other cell types. TNF is pleiotropic, induces cytotoxicity, cachexia, and septic shock, shows anti-viral, anti-inflammatory, and immunoregulatory activities, and stimulates the growth of certain cells. Two different receptors, termed p60 (also known as p55 or TNFR-I) and p80 (also known as p75 or TNFR-II), bind TNF with high affinity. The extracellular domain of both the p60 and p80 forms of the TNF receptor share 28% sequence identity with each other and other members of the TNF/nerve growth factor (NGF) receptor family. Little homology exists between the cytoplasmic domains of p60 and p80 forms of the TNF receptor.

Intracellular events linking the activation of TNF receptors to specific cellular responses are unclear. TNF activates the transcriptional complex nuclear factor kappa B (NFkB) within minutes, transmitting a signal from the receptor to the nucleus. Additionally, a TNF signaling pathway involving the breakdown of sphingomyelin to ceramide and stimulation of a ceramide-activated kinase have been described. TNF augments the phosphorylation state of several proteins such as the small heat shock protein (hsp 27), the eukaryotic initiation factor 4E, the inhibitory subunit of NF-κB (IκB-α), and the epidermal growth factor receptor. Various protein kinase activities have been demonstrated to be rapidly and transiently activated upon TNF treatment.

The functional role of the cytoplasmic domain of p60 for signaling the cytotoxic response to TNF has been reported. Brakebusch et al. expressed a series of truncated human p60 receptors in murine L929 cells and observed that deletion of 50% of the cytoplasmic domain resulted in the loss of the TNF cytotoxic effect but not shedding of the receptor. Similarly, Tartaglia et al. demonstrated that expression of human p60 lacking most of the cytoplasmic domain rendered L929 cells defective in TNF responses. Additionally, Tartaglia et al. showed that a region within the cytoplasmic domain of p60 termed the "death domain" (residues 324–426) was necessary for generation of the TNF cytotoxic signal in mouse L929 cells. Thus, the cytoplasmic domain may contain structural information necessary for interaction with intracellular components required for TNF signaling.

Receptors that lack kinase activity transmit their signals through recruitment of specific kinases by their cytoplasmic domains. However, there has been no evidence of any proteins in association with the cytoplasmic domain of either the p60 or the p80 forms of the tumor necrosis factor receptor. Manipulation of such a protein would provide an avenue for regulation of TNF's biological activities.

In spite of the conserved features of the extracellular domains of the p60 and p80 forms of the tumor necrosis factor receptor, it has been difficult to identify common motifs in their intracellular regions. Like other members of the TNF/NGF receptor family, the p60 and p80 forms of the TNF receptor do not contain consensus sequences characteristic of tyrosine or serine/threonine kinases, or any other signal transduction motifs. However, ligand binding to the TNF receptor activates a wide variety of putative second-messenger events, including a rapid increase in protein phosphorylation. It is unclear which of these processes form the link between ligand binding at the cell-surface and the profound effects that TNF has upon cell function.

Efforts to identify receptor domains critical for cellular signaling have relied on mutational analysis. The deletion analysis reported by Brakebusch et al. indicated that truncation of at least half of the cytoplasmic domain of p60 abolished the ability of TNF to signal for cytotoxicity. Additionally, a mutant receptor lacking most of its cytoplasmic domain interfered with the endogenous wild-type receptor, suggesting that receptor clustering is necessary for signal transmission. Similarly, Tartaglia et al. demonstrated that the expression of a truncated human p60 receptor in mouse cells suppressed the signaling of the endogenous mouse TNF receptors in response to the ligand. Interestingly, the death domain shares weak homology with a region found in the cytoplasmic domain of the Fas antigen that is necessary for apoptotic signal transduction.

The prior art is deficient in the lack of effective means of inhibiting the various biological activities of tumor necrosis factor. The present invention fulfills this longstanding need and desire in the art.

SUMMARY OF THE INVENTION

The present invention identify proteins that associate with the cytoplasmic domain of the p80 form of the TNF receptor. The present invention provides evidence of physical and functional association of a novel protein kinase that interacts with the cytoplasmic domain of the p80 form of the TNF receptor.

In one embodiment of the present invention, there is provided an isolated and purified protein that associates with the cytoplasmic domain of the p80 form of the tumor necrosis factor receptor, having a molecular weight of 59 kDa on SDS-PAGE, is a phosphoprotein, and does not bind to the p60 form of the tumor necrosis factor receptor. The protein of the present invention is termed herein Tumor Necrosis Factor Receptor-II Associated Protein (p80TRAP).

In another embodiment of the present invention, there is provided an isolated and purified protein kinase that associates with the cytoplasmic domain of the p80 form of the tumor necrosis factor receptor, said kinase phosphorylates both the p80 and p60 forms of the tumor necrosis factor receptor and phosphorylates a 59 kDa molecular weight protein associated with the cytoplasmic domain of the p80 form of the tumor necrosis factor receptor. The kinase of the present invention is termed herein Tumor Necrosis Factor Receptor-II Associated Kinase (p80TRAK).

In yet another embodiment of the present invention, there is provided a pharmaceutical composition comprising an competitive inhibitor of the kinase or p80TRAK of the present invention and a pharmaceutically acceptable carrier.

In yet another embodiment of the present invention, there is provided a method of treating a pathophysiological state characterized by an undesirable physiological level of tumor necrosis factor comprising the step of administering a pharmacologically effective dose of the pharmaceutical composition to a human.

In other embodiments of the present invention, there are provided various methods of decreasing the biological effects of tumor necrosis factor and reducing the cytotoxic effects of tumor necrosis factor.

The cytoplasmic domain of the p80 tumor necrosis factor receptor associates with a serine/threonine kinase, termed p80TRAK, that phosphorylates both the p60 and p80 forms of the receptor. Deletion mutants of the p80 cytoplasmic domain were constructed to determine the minimal region for binding p80TRAK. p80TRAK bound p80 wild type containing residues 266–439, p80Δ2 (354–439), p80Δ3 (295–397), p80Δ5 (354–397), and to a lesser extent p80Δ6 (382–439), but not glutathione-S-transferase, p80Δ1 (266–353), or p80Δ4 (295–353), thus implying that residues 354–397 (p80Δ5) in the p80 cytoplasmic domain are sufficient for p80TRAK binding. Phosphoamino acid analysis of p80Δ5 revealed phosphorylation primarily on serine residues. Like p80TRAK, among the six deletions analyzed, only one, p80Δ5 (residues 354–397) was found to be sufficient for binding and phosphorylation by purified casein kinase 1 in vitro. Additionally, a casein kinase 1-specific inhibitor, casein kinase 1–7, inhibited p80TRAK activity as measured by phosphorylation of p80Δ5. Thus, the present invention also shows that p80TRAK associates with a short stretch of ~44 residues located in the cytoplasmic domain of the p80 tumor necrosis factor receptor and that this kinase is related to casein kinase 1.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

The following abbreviations are used in the instant specification: TNF: tumor necrosis factor; NGF: nerve growth factor; NF-κB: nuclear factor kappa B; IκB-α: inhibitory subunit of NF-κB; FBS: fetal bovine serum; PCR: polymerase chain reaction; MBP: myelin basic protein; GST: glutathione-S-transferase; CD: cytoplasmic domain; PMSF: phenylmethylsulfonyl fluoride; SDS: sodium dodecyl sulfate; PAGE: polyacrylamide gel electrophoresis; PVDF: polyvinylidene difluoride; TLC: thin layer chromatography; p80TRAK: tumor necrosis factor receptor-associated kinase; and p80TRAP: tumor necrosis factor receptor-associated protein.

FIG. 3 shows the characterization of GST-p80CD-associated kinase activity. Binding of U-937 cell extracts (2×10$^6$) to GST-p80CD was determined.

FIG. 8 shows deletions of the cytoplasmic domain of the p80 tumor necrosis factor receptor.

FIG. 8b shows a phosphoamino acid analysis of p80WT and p80Δ5 was performed as previously described above. The positions of phosphoserine, -threonine, and -tyrosine was indicated by staining the TLC plate with ninhydrin.

DETAILED DESCRIPTION OF THE INVENTION

Figure 1:
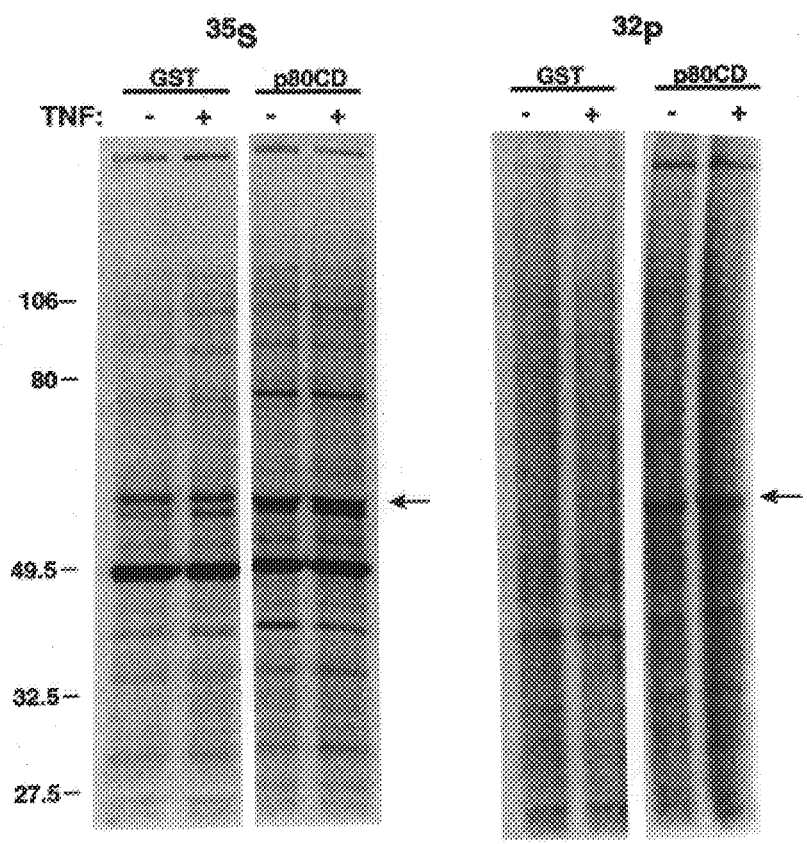
FIG. 1 shows the association of proteins with GST-p80CD from $^{35}$S-labeled (left) and $^{32}$P-labeled (right) U-937 cells. Left, U-937 cells (4×10$^6$/ml) were labeled for 4 hours at 37° C. with a mixture of $^{35}$S methionine/cysteine (50 μCi/ml) in 30 ml of methionine/cysteine-free RPMI-1640 medium supplemented with 10% dialyzed FBS. Cells were collected, washed 3× with RPMI-1640, adjusted to 1.5×10$^6$/ml, and incubated at 37° C. for 1 hour. Cells were treated with 5 nM TNF for 5 minutes, washed 2× with cold phosphate-buffered saline, lysed, and cell extracts allowed to bind to GST and GST-p80CD. Adsorbed proteins were subjected to 7.5% SDS-PAGE, and the dried gel was analyzed by a Phosphorimager. Molecular masses in kDa are as indicated; the arrow indicates the position of the 59-kDa protein. Right, U-937 cells (4×10$^6$/ml) were labeled for 2 hours with carrier-free [$^{32}$P]orthophosphate (500 μCi/ml) in 30 ml of phosphate-free RPMI-1640. Cells were washed 3× with fresh medium, treated with 5 nM TNF for 5 minutes.

The present invention is directed to a composition of matter comprising an isolated and purified protein that associates with the cytoplasmic domain of the p80 form of the tumor necrosis factor receptor, having a molecular weight of 59 kDa as determined by SDS-PAGE, is a phosphoprotein, and does not bind to the p60 form of the tumor necrosis factor receptor. Moreover, this phosphoprotein of the present invention is phosphorylated at serine and threonine residues and exhibits optimal phosphorylation in the presence of $Mn^{2+}$, and to a lesser extent, $Mg^{2+}$.

The present invention is also directed to an isolated and purified protein kinase that associates with the cytoplasmic domain of the p80 form of the tumor necrosis factor receptor, said kinase phosphorylates both the p80 and p60 forms of the tumor necrosis factor receptor and phosphorylates the 59 kDa molecular weight protein of the present invention that is associated with the cytoplasmic domain of the p80 form of the tumor necrosis factor receptor.

It is specifically contemplated that pharmaceutical compositions may be prepared using the novel protein of the present invention. In such a case, the pharmaceutical composition comprises the novel protein of the present invention and a pharmaceutically acceptable carrier. A person having ordinary skill in this art would readily be able to determine, without undue experimentation, the appropriate dosages and routes of administration of the novel protein of the present invention. Accordingly, the present invention also comprises a pharmaceutical composition comprising an competitive inhibitor of the kinase of the present invention and a pharmaceutically acceptable carrier.

The present invention also comprises a method of decreasing the biological effects of tumor necrosis factor comprising the step of inhibiting the phosphorylation of the p80TRAP protein of the present invention. Accordingly, the p80TRAP protein of the present invention is inhibited by administering a pharmacologically effective dose of the pharmaceutical composition of the present invention. Further, the present invention includes a method of decreasing the biological effects of tumor necrosis factor comprising the step of inhibiting the p80TRAK kinase and a method of reducing the cytotoxic effects of tumor necrosis factor comprising the step of inhibiting the p80TRAK kinase.

In another embodiment, the present invention is directed to a method of treating a pathophysiological state characterized by an undesirable physiological level of tumor necrosis factor comprising the step of administering a pharmacologically effective dose of the pharmaceutical composition of the present invention to a human.

Generally, the pathophysiological state or conditions treated by the methods of the present invention is any state in which inhibition of the biological effects of tumor necrosis factor is desirable. Accordingly, the pathophysiological states or conditions treated may be ones in which the physiological concentrations of TNF and consequently, the biological effects, are undesirably high. Alternatively, the methods of the present invention may be used to treat pathophysiological state where the level of TNF is "normal" but a reduction or inhibition of the physiological effects of TNF is therapeutically desirable. It is also contemplated that the methods of the present invention may be useful in treating "normal" states or conditions where a reduction or inhibition of the physiological effects of TNF is therapeutically desirable.

Thus, the methods of the present invention may be used to treat such conditions as neoplastic diseases, the human immunodeficiency disease, sepsis, cachexia, graft vs host disease, autoimmune diseases, cerebral malaria and capillary leak syndrome. Representative examples of neoplastic diseases include leukemias, ovarian carcinoma, renal cell carcinoma, breast adenocarcinoma and glioblastoma. Representative examples of autoimmune diseases include systemic lupus erythematosus, rheumatoid arthritis and multiple sclerosis.

In another embodiment, the present invention is directed to a method of treating a neuro-oncologic state, comprising administering to a human a pharmacologically effective dose of the pharmaceutical composition of the present invention. Preferably, the neuro-oncologic state is glioblastoma, an astrocytoma or a meningioma. Also provided by the present invention is a method of treating renal cancer comprising administering to a human a pharmacologically effective dose of the pharmaceutical composition of the present invention.

The level of ordinary skill of the average scientist in the area of molecular cell biology has increased substantially in recent years. A person having ordinary skill in this art would readily be able to sequence the phosphoprotein (p80TRAP)

and protein kinase (p80TRAP) of the present invention, given the teachings herein.

With knowledge of the teachings of the present invention, a person having ordinary skill in this art would readily be able to prepare specific competitive inhibitors of the protein kinase of the present invention. That is, a person having ordinary skill in this area of research would be readily able to localize the phosphorylation site on the substrate phosphorylated by the kinase and subsequently use this knowledge to develop competitive inhibitors of the kinase.

The following examples are given for the purpose of illustrating various embodiments of the invention and are not meant to limit the present invention in any fashion.

EXAMPLE 1

Materials

Human TNF ($5 \times 10^7$ units/mg) was a gift of Genentech (South San Francisco, Calif.). All reagents were reagent grade or higher. The histiocytic lymphoma cell line U-937 (CRL 1593) was obtained from the ATCC. Cells were grown in RPMI-1640 medium supplemented with 10% FBS and 100 µg/ml streptomycin at 37° C. in a 5% $CO_2$ incubator. *Escherichia coli* strain BL21 was a gift of Dr. V. W. Rodwell (Purdue University, W. Lafayette, Ind.). *E. coli* strain NM522 and plasmid pGEX-2TH were gifts of Dr. H. Saya (M. D. Anderson Cancer Center, Houston, Tex.). The plasmid containing the entire coding sequence of p80 (pCMVXVBpL4-p80) was a gift from Dr. T. Kohno (Synergen, Boulder, Colo.). Construction of the plasmid encoding GST-p60CDΔ1 was as follows:

Construction of Glutathione-S-Transferase (GST) Expression Vectors

DNA manipulations were carried out as described by Sambrook et al., (1989) *Molecular cloning: A Laboratory Manual*, 2nd ed., Cold Spring Harbor Laboratory Press, Cold Spring Harbor, N.Y. Polymerase chain reaction (PCR) and specific 5' and 3' primers with unique restriction sites were used to amplify the cytoplasmic domain of p60 from pCMVXVBpL4-p60 for insertion into the GST fusion vectors. The PCR primers were:

5'-CTAAGAGAATTCGCTACCAACGGTGGAAGT-CC-3' (SEQ ID NO.1) and

5'-GACGTACTCGAGTCATCTGAGAAGACT-3' (SEQ ID NO.2)

and were used to amplify a 671-bp fragment that encodes residues Y207 to R426 of p60. The PCR fragment was digested with EcoRI and XhoI and ligated into EcoRI/XhoI-digested pGEX-KG to give rise to pGEX-KG-p60CD. The pGEX-KG-p60CD was digested with EcoRI and partially digested with HindIII, and both the 700-bp (EcoRI/HindIII fragment) and the 570-bp (HindIII/HindIII due to an internal HindIII site in the p60 gene) fragments were isolated. The 700-bp EcoRI/HindIII fragment was inserted into EcoRI/HindIII-digested pGEX-2TH and termed pGEX-2TH-p60CD. In order to place the p6CD coding sequence in frame with GST, pGEX-2TH-p60CD was further digested with BamHI, filled in with Klenow, and religated to give rise to pGEX-2THΔB-p60CD. Additionally, the 570-bp HindIII/HindIII fragment was inserted into HindIII-digested pGEX-2THΔB to give pGEX-2THΔB-p60CDΔ1.

EXAMPLE 2

Construction, Expression, and Purification of GST Fusion Protein

All subsequent DNA manipulations were carried out as described by Sambrook et al. Molecular Cloning: A Laboratory Manual, 2nd ed., Cold Spring Harbor Laboratory Press, Cold Spring Harbor, N.Y. PCR and the primers 5'-CTAAGAGGATCCAAAAAGAAGCCCTTGTG-CCTG-3' (SEQ ID NO.3) and 5'-TCTTAGAAGCTTTTAACTGGGCTTCATCCCA-GC-3' (SEQ ID NO.4) with unique restriction sites were used to amplify a 546-bp fragment from pCMVXVBpL4-p80 for insertion into pGEX-2TH. This construct, pGEX-2TH-p80CD, expresses a fusion protein (GST-p80CD) with the p80 cytoplasmic domain (K266-S439) linked to GST. Expression of GST-p80CD in BL21 cells and purification were carried out as follows: BL21 cells harboring the expression plasmid were induced with 0.5 mM IPTG at 37° C. for one hour. Cells were collected by centrifugation and lysed in Buffer A (20 mM Tris, pH 8.0, 200 mM NaCl, 10% glycerol, 0.5% NP-40, 1 mM PMSF, 2 µg/ml aprotinin, 2 µg/ml leupeptin, 0.1% 2-mercaptoethanol) containing 5 mg lysozyme and briefly sonicated. The lysate was cleared by centrifugation at 30,000 rpm and the supernatant passed once through a 1.2 ml column of 50% (v/v) glutathione-agarose. The column was subsequently washed with 20 ml Buffer A, 10 ml of 1M NaCl in Buffer A and 20 ml Buffer A. The protein was stored at 4° C. on glutathione-agarose beads as a 50% slurry in Buffer A (20 mM Tris, pH 8.0, 200 mM NaCl, 10% glycerol, 0.5% NP-40, 1 mM PMSF, 2 µg/ml aprotinin, 2 µg/ml leupeptin, and 0.1% 2-mercaptoethanol. The amount of fusion protein was estimated by Coomassie Blue staining of SDS-PAGE.

EXAMPLE 3

In Vitro Binding of GST Fusion Protein to Cell Extracts

U-937 cells were treated as described above and lysed in 1 ml of lysis buffer (20 mM Tris, pH 7.7, 0.5% NP-40, 200 mM NaCl, 50 mM NaF, 0.2 mM sodium orthovanadate, 1 mM PMSF, 2 µg/ml aprotinin, 2 µg/ml leupeptin, and 0.1% 2-mercaptoethanol) on ice for 10 minutes followed by 10 minutes of centrifugation. The supernatant was precleared with 25 µg GST and 50 µl 50% (v/v) glutathione-agarose for 2–12 hours at 4° C. The precleared supernatant was mixed with approximately 5–10 µg GST-p80CD that is bound to gluththione-agarose for 2 hours at 4° C. The beads were collected by centrifugation and washed extensively with lysis buffer (4×500 µl) and with kinase buffer (3×500 µl: 20 mM HEPES, pH 7.4, 10 mM NaF, 0.2 mM sodium orthovanadate, and 0.1% 2-mercaptoethanol). The pellets were then used for in vitro kinase assays.

EXAMPLE 4

In Vitro Kinase Assays

Standard kinase assays were carried out for 10 minutes at 37° C. in 50 µl containing 20 mM HEPES, pH 7.4, 10 mM $MgCl_2$, 0.2 mM ATP, 0.2 mM NaF, 0.1 mM sodium orthovanadate, and 10 µCi [γ-$^{32}$P]ATP or as described. Reactions were stopped with 15 µl SDS-sample buffer, boiled for 5 minutes and then subjected to SDS-PAGE. Protein bands were visualized by staining with Coomassie Blue and the dried gels were analyzed by a Phosphorimager (Molecular Dynamics, Sunnyvale, Calif.). Labeled protein bands were quantitated by using ImageQuant Software (Molecular Dynamics, Sunnyvale, Calif.).

EXAMPLE 5

Phosphoamino Acid Analysis

Samples subjected to in vitro kinase assays were separated by SDS-PAGE, transferred to PVDF membranes by electrophoresis, and stained with Ponceau S. Protein bands were excised, boiled with 6N HCl for 1 hour, dried by speed vacuum, and analyzed by TLC in buffer containing 80% methanol, 1.5% acetic acid, and 0.5% formic acid. Subsequently, the dried TLC plate was analyzed by a Phosphorimager. Migration of standards was visualized by spraying the dried TLC plate with ninhydrin.

EXAMPLE 6
Protein kinase associated with the p80 form of the TNF receptor

The present invention identifies proteins and protein kinase from U-937 cells that associate with the p80 cytoplasmic domain of the TNF receptor. Whether the cytoplasmic domain of p80 form of the tumor necrosis factor receptor could interact with proteins from either $^{35}$S-methionine/cysteine or $^{32}$P$_i$-labeled U-937 cells was first examined. Irrespective of TNF treatment, a protein was found to associate specifically with GST-p80CD in $^{35}$S-labeled cells (FIG. 1, left). This protein, which had an approximate molecular mass of 58±2 kDa, was detected in six separate studies.

To determine whether phosphoproteins could bind to GST-p80CD, cells were labeled with $^{32}$P$_i$. The present invention identified a phosphoprotein of approximately 60±1 kDa (average of four studies) that bound to GST-p80CD (FIG. 1, right). In three of the four studies, the amount of phosphorylation of the associated phosphoprotein was increased when cells were treated with TNF. Thus, the protein identified by $^{35}$S-labeling was a phosphoprotein referred here on as pp59 and for the purposes of the present invention is termed p80TRAP as defined above.

A previous report indicated that overexpression of the p80 form of the human TNF receptor in the human embryonic kidney cell line 293 is constitutively phosphorylated on serine (97%) and threonine (3%) residues. Others have reported phosphorylation of the natural p80 TNF receptor on serine residues from SW480T cells. Although these reports show that the p80 receptor was phosphorylated in vivo, no kinase has been shown to be associated with this receptor. The present invention indicates that GST-p80CD serves as a substrate for several purified protein kinases.

EXAMPLE 7
Phosphorylation of fusion protein

Figure 2:
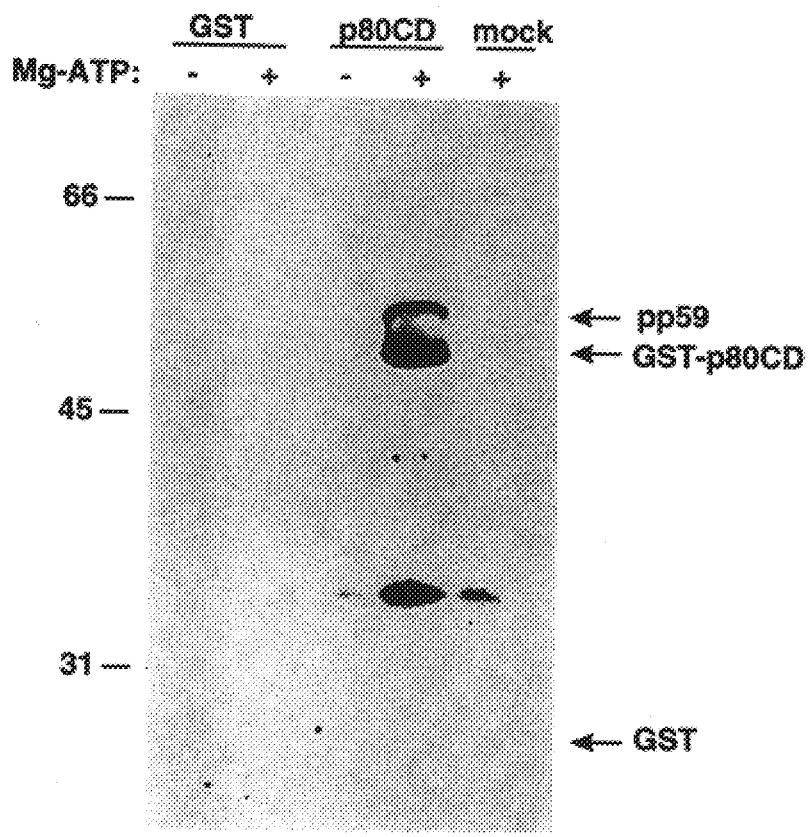
FIG. 2 shows the kinase activity associates and phosphorylates GST-p80CD. Cells (2×10$^6$) were lysed and in vitro binding to 5 μg of either GST or GST-p80CD was determined. For in vitro kinase reactions, samples were incubated in the absence (−) or presence (+) of Mg-ATP for 10 minutes at 37° C. In the mock reaction, no cell extract was added. Proteins were subjected to 10% SDS-PAGE and visualized by staining with Coomassie Blue. The dried gel was analyzed by a Phosphorimager.

Employing the GST fusion protein system, the present invention shows that a protein kinase from U-937 cells associates with the cytoplasmic domain of the p80 form of the TNF receptor. As defined above, this kinase is termed p80TRAK for the purposes of the present invention. FIG. 2 shows that GST-p80CD bound to glutathione-agarose adsorbed protein kinase from cell extracts that phosphorylated the fusion protein in a Mg-ATP-dependent manner. Under these conditions, neither kinase was found to be associated with GST alone nor was phosphorylated (FIG. 2). A mock reaction devoid of cell extracts showed that the kinase activity originated from the cells and that the cytoplasmic domain had no intrinsic kinase activity. The fusion protein could be cleaved with thrombin (at a cleavage site between GST and p80CD) to show that only the cytoplasmic domain of p80 form of the TNF receptor was phosphorylated. Additionally, after in vitro kinase assays, a specific protein of approximately 59 kDa bound to GST-p80CD and was phosphorylated (FIG. 2). Based on molecular size, this 59-kDa protein appears to be the same protein that was identified in both $^{35}$S- and $^{32}$P-labeled cells (FIG. 1). Furthermore, the cytoplasmic domain of the p60 receptor did not bind pp59 the protein (p80TRAP). The phosphorylation of a second smaller protein was most likely due to a degradation.

EXAMPLE 8
Phosphorylation of p80TRAP

Figure 3A:
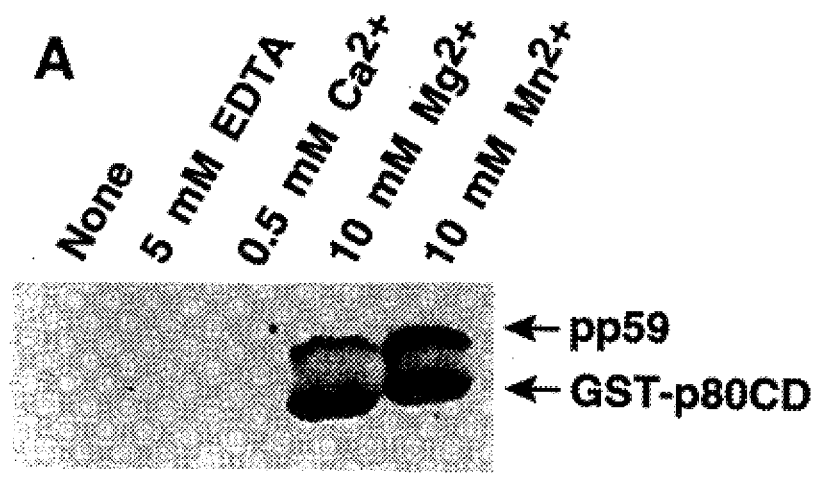
FIG. 3A shows that the in vitro kinase assays were performed on proteins adsorbed to GST-p80CD with the indicated cation concentrations for 10 minutes at 37° C.
Figure 3B:
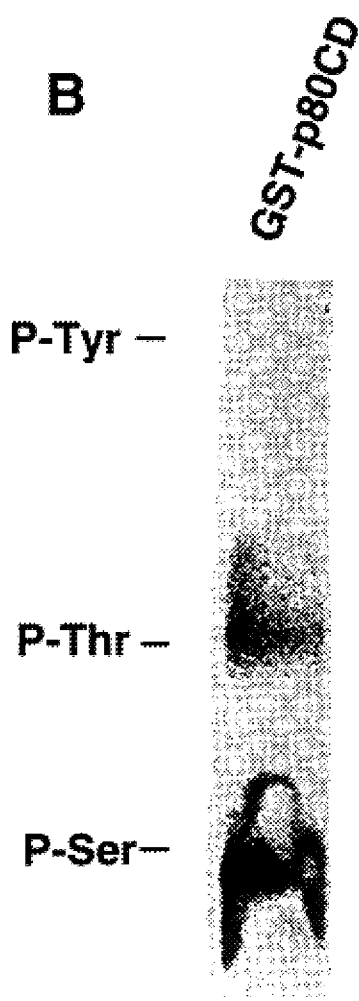
FIG. 3B shows that after in vitro kinase assay, phosphoamino acid analysis of GST-p80CD was performed. The migrations of phosphoamino acid standards are shown.
Figure 7:
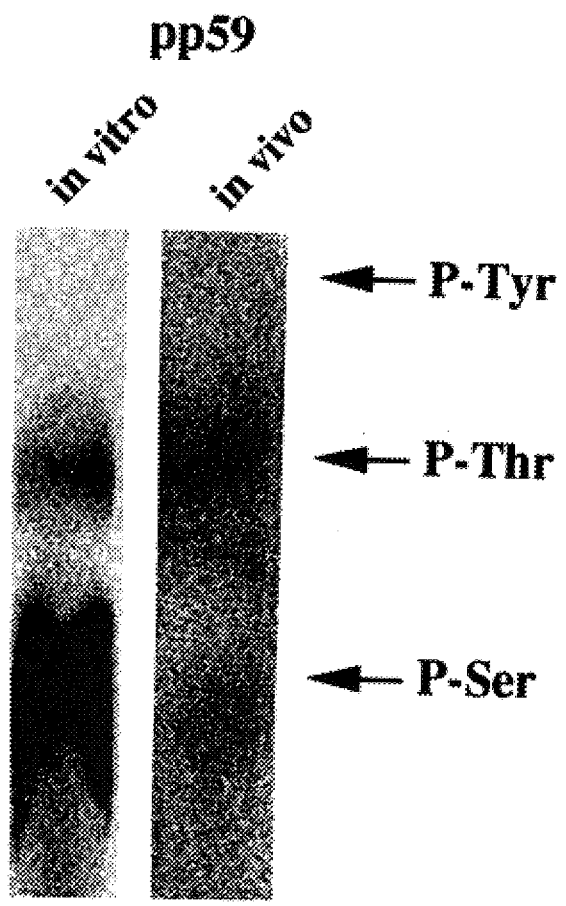
FIG. 7 shows a phosphoamino acid analysis of pp59 or p80TRAP phosphorylated in vitro and in vivo. In vivo and in vitro phosphorylation of pp59 or p80TRAP was performed as described above, except that the SDS-PAGE gel was transferred to PVDF by electrophoresis, p80TRAP was excised from the filter and subjected to phosphoamino acid analysis as described above.

The p80 form of the TNF receptor cytoplasmic domain-associated kinase activity was found to be optimal only in the presence of either Mg$^{++}$or Mn$^{++}$, but not Ca$^{++}$(FIG. 3A). Phosphorylation of p80TRAP also preferred Mn$^{++}$over Mg$^{++}$. Unlike reports that showed phosphorylation of p80 form of the TNF receptor primarily at serine, phosphoamino acid analysis in the present invention indicates that the phosphorylation of the p80 form of the TNF receptor occurred on serine and threonine residues (FIG. 3B). Phosphorylation of p80TRAP, both in vitro and in vivo, was also found to occur on serine and threonine residues (FIG. 7), suggesting that the p80 cytoplasmic domain-associated kinase phosphorylates p80TRAP in vivo.

Figure 3C:
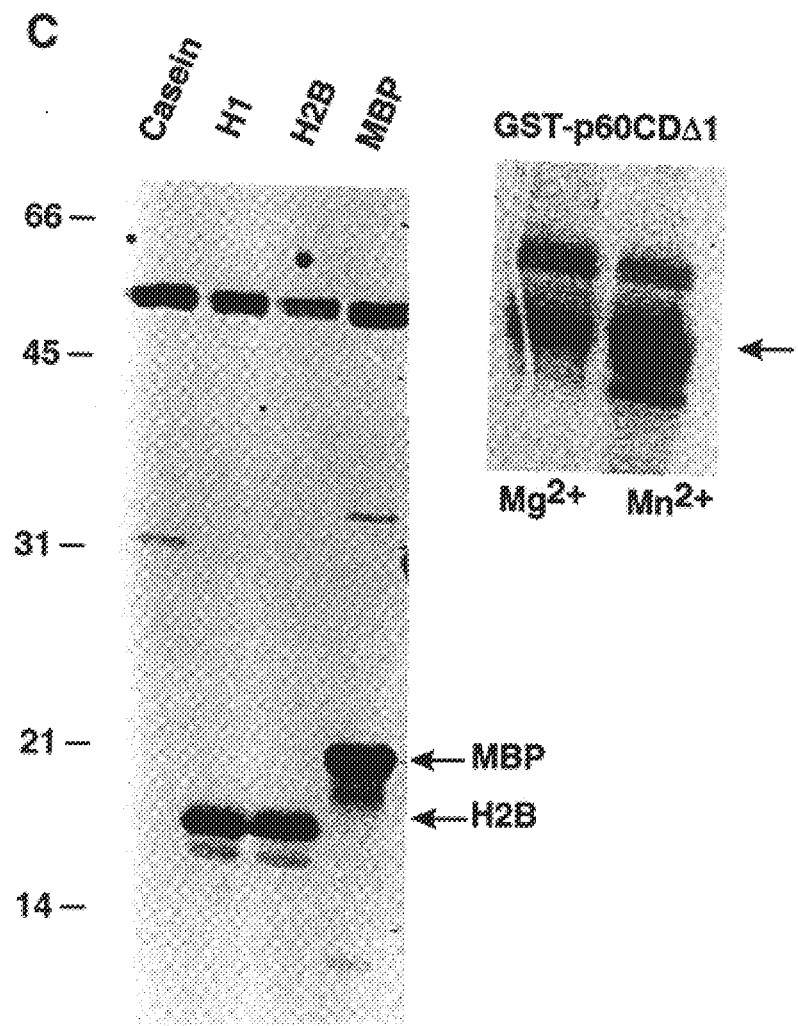
FIG. 3C shows that the in vitro kinase assays were performed with 10 mM MgCl$_2$ (left) or 10 mM MgCl$_2$ or MnCl$_2$ (right) and the corresponding substrates for 10 minutes at 37° C. and subjected to 12% (left) or 7% (right) SDS-PAGE. Arrows indicate positions of proteins after staining with Coomassie Blue. Shown are phosphorimages of the dried gels.

Besides phosphorylating p80TRAP and the cytoplasmic domain of p80, the receptor-associated kinase (p80TRAK) also phosphorylated histone H2B and MBP (FIG. 3C). Interestingly, the p80 receptor-associated kinase could also phosphorylate the cytoplasmic domain of the p60 form of the TNF receptor (FIG. 3C). Thus, there exists a novel cross-talk between the two forms of the TNF receptor and that these two receptors bind distinct protein kinases.

EXAMPLE 9
Time-dependency of phosphorylation

Figure 4:
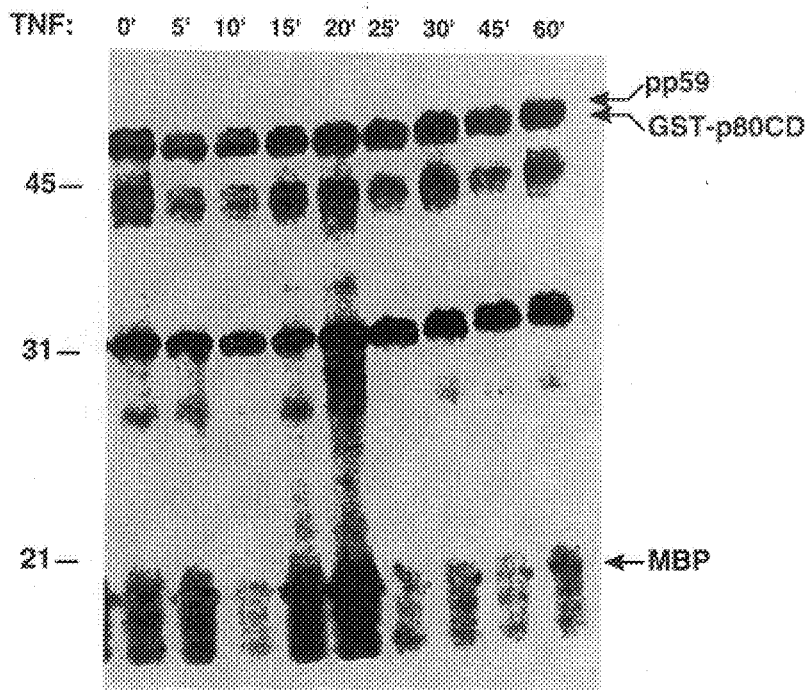
FIG. 4 shows that the p80 receptor-associated kinase activity is increased by TNF treatment. Serum-starved U-937 cells (2×10$^6$) were incubated with 5 nM TNF for the indicated time. In vitro binding to GST-p80CD and kinase assays in the presence of 10 mM MgCl$_2$ and MBP were performed as described below. Proteins were subjected to 12% SDS-PAGE; a phosphorimage of the dried gel is shown.

It is known that the treatment with TNF of A293 cells overexpressing the p80 receptor yield no change in p80 receptor phosphorylation. In addition, pretreatment of SW480T cells with staurosporine reduced the extent of phosphorylation of the p80 receptor suggesting, albeit indirectly, that a staurosporine-sensitive kinase(s) was being inhibited. The present invention demonstrates that TNF could induce the GST-p80CD-associated kinase activity from U-937 cells. Serum-starved U-937 cells treated with 5 nM TNF for various times were subjected to in vitro binding assays with GST-p80CD, followed by kinase reactions with Mg$^{++}$and MBP. TNF-dependent phosphorylation of MBP peaked between 15–25 minutes with approximately a 2-fold increase from time zero (FIG. 4). This was observed in at least three separate experiments. Cells left untreated showed a basal level of p80 receptor-associated kinase activity with myelin basic protein as the substrate. In addition, both GST-p80CD and p80TRAP showed elevated levels of phosphorylation coincident with increased phosphorylation of myelin basic protein (FIG. 4). In the present invention, the p80 receptor-associated kinase activity in vitro was measured in a time-dependent manner, whereas prior art experiments measured the phosphorylation of immunoprecipitated p80 receptor in vivo after 15 to 30 minutes treatment with TNF. Additionally, the p80 form of the tumor necrosis factor receptor may not be the optimum substrate for the associated kinase, as illustrated by the phosphorylation of myelin basic protein (FIG. 4).

The cytoplasmic domain of p80 receptor comprises 174 amino acids and is shorter by 48 amino acids than the p60 cytoplasmic domain. Similar to the p60 receptor, the cytoplasmic domain of p80 contains a high content of proline, serine, threonine, and acidic residues; however, these are not clustered in regions as in the p60 receptor. Unlike the p60 receptor, the p80 receptor lacks tyrosine residues in its intracellular region.

EXAMPLE 10
Purification of p80TRAK

Figure 5:
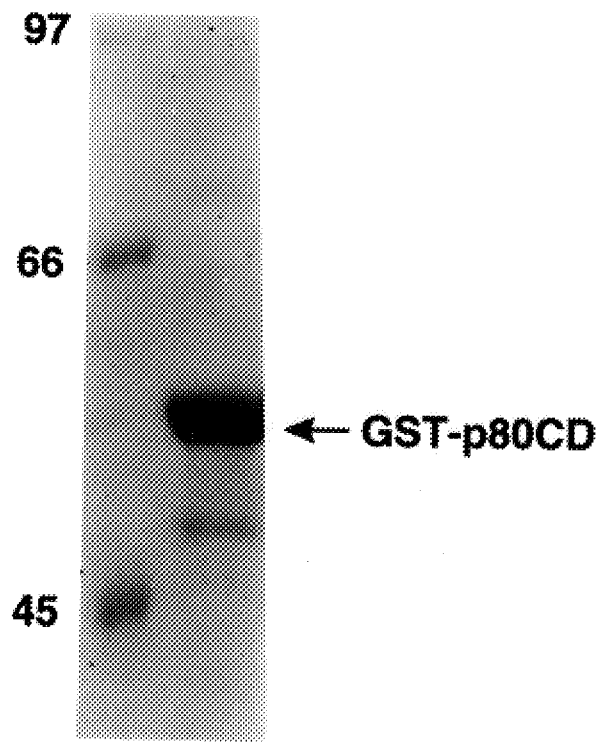
FIG. 5 shows a SDS-PAGE of purified GST-p80CD. Molecular mass standards of the indicated size, expressed in kDa, and approximately 10 μg of purified GST-p80CD were subjected to 7.5% SDS-PAGE. The gel was stained with Coomassie Blue.
Figure 6:
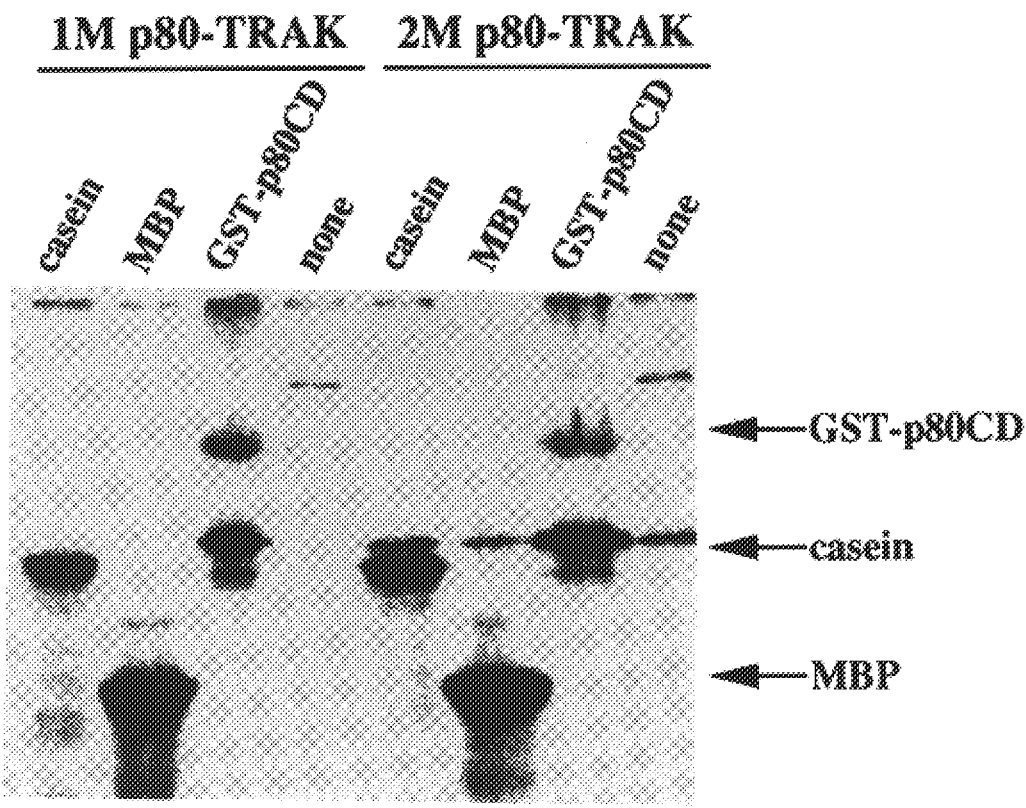
FIG. 6 shows the results of in vitro kinase assays of 1M and 2M NaCl elutions of p80-TRAK with casein, MBP, and GST-p80CD as substrates. Standard kinase assays were performed with a 5 μl portion of the 1M and 2M elutions with the indicated substrate. Proteins were subjected to 12% SDS-PAGE, the protein bands were visualized by staining with Coomassie Blue and the dried gel was analyzed by a PhosphorImager.

Approximately 14.5×10$^9$ U937 cells were grown to a density of 1.4×10$^6$ cells/ml in 10.5 L of RPML-1640 medium in the presence of 10% FBS. Cells were collected by centrifugation, washed three times with 50 ml cold PBS and lysed in approximately 120 ml lysis buffer for 30 minutes on ice. The lysate was cleared by centrifugation at 8000 rpm for 10 minutes at 4° C. in a SS34 rotor. The supernatant was mixed with 1 mg of GST attached to glutathione-agarose beads overnight at 4° C. with rocking. Next, the mixture was centrifuged at 3000 rpm for 10 minutes and the supernatant was mixed with 500 µl of a 50% slurry of GST-p80CD attached to glutathione-agarose beads for 4 hours at 4° C. The mixture was centrifuged and equal volumes of the beads were transferred to 10 eppendorf tubes. The beads were washed by the following method and each wash was saved: six washes (600 µl each) of lysis buffer, five washes (600 µl each, 5 minutes rocking in between each wash) of 1M NaCl in lysis buffer and five washes (600 µl each, 10 minutes rocking in between each wash) of 2M NaCl, 10 mM EDTA in lysis buffer. Subsequently, each of the five tubes were washed onto a column with two washes (500 µl) and washed on the column with 1 ml of 2M NaCl, 10 mM EDTA in lysis buffer followed by 1.5 ml lysis buffer. The 1M and 2M salt washes were concentrated and the buffer exchanges to a buffer consisting of 20 mM HEPES, 50 mM NaCl, 10% glycerol, 0.1% 2-mercaptoethanol, 10 mM NaF and 0.2 mM sodium orthovanadate. Kinase assays were performed with casein, MBP and GST-p80CD as substrates. FIG. 5 shows that th cytoplasmic domain of the p80 (residues 266–439) was expressed in *E. coli* as a GST fusion protein and purified by affinity chromatography on glutathione agarose. The fusion protein has a molecular mass of approximately 54 kDa. FIG. 6 shows that the p80TRAK was purified using an in vitro binding assay with GST-p80CD attached to glutathione-agarose as an affinity column as described above. The p80TRAK was found to elute from the affinity column in two elutions of 1M and 2M NaCl. The kinase activity was measured by using casein, MBP and GST-p80CD as substrates (FIG. 6).

EXAMPLE 11
Materials

The histiocytic lymphoma cell line U-937 (CRL 1593) was obtained from the American Type Culture Collection (Rockville, Md.) and maintained in a 5% $CO_2$ atmosphere at 37° C. in RPMI-1640 medium supplemented with 10% fetal bovine serum and penicillin-streptomycin, all obtained from Life Technologies, Inc. (Grand Island, N.Y). Purified casein kinase 1 was purchased from New England Biolabs, Beverly, Mass. The casein kinase 1 (CK1)-specific inhibitor casein kinase 1 (CK1)-7 was purchased from Seikagaku America Inc., Rockville, Md.

EXAMPLE 12
Construction, Expression, and Purification of glutathione-S-transferase Fusion Protein All subsequent DNA manipulations were carried out as described by Sambrook et al. (15). FIG. 8 illustrates the fusion proteins that were made. The 5'-primers CTAAGAG-GATCCAAAAAGAAGCCCTTGTGCCTG (WT, Δ1), CTAAGAGGATCCGGGACCCAGGTCAATGTCACC (Δ2, Δ5), CTAAGAGGATCCCAGCACCTGCTGATCA-CAGCG (Δ3, Δ4), and CTAAGAGGATCCACAATGG-GAGACACAGATTCC (Δ6), and the 3'-primers TCTTA-GAAGCTTTTAACTTGGGCTTCATCCCAGC (WT, Δ2, Δ6) (SEQ ID NO.5), TCTTAGAAGCTTTTAATGGCCAC-CAGGGGAAGA (Δ1, Δ4) (SEQ ID NO.6), and TCTTA-GAAGCTTTTACTCGTCCTTCGGGGAACTC (Δ3, Δ5) (SEQ ID NO.7) were used to amplify fragments from pCMVXVBpL4-p80 (SEQ ID NO.8) with unique restriction sites (SEQ ID NO.9) using polymerase chain reaction. The polymerase chain reaction products were digested with BamHI/HindIII (SEQ ID NO.10) and inserted into digested pGEX-2TH (SEQ ID NO.11) to yield the appropriate expression vector. Expression and purification of the glutathione-S-transferase fusion proteins from BL21 cells were carried out as previously described (14).

EXAMPLE 13
In vitro Binding and Kinase Assays with glutathione-S-transferase Fusion Proteins U-937 cells ($2 \times 10^6$) were lysed in 600 µl of lysis buffer (20 mM HEPES, pH 7.4, 0.1% NP-40, 250 mM NaCl, 10 mM NaF, 1 mM phenylmethylsulfonyl fluoride, 2 µg/ml aprotinin, and 2 µg/ml leupeptin) on ice for 30 minutes and then centrifuged for 10 minutes. The supernatant was adjusted to 125 mM NaCl by addition of lysis buffer without NaCl and precleared with 10 µg of glutathione-S-transferase bound to glutathione-agarose beads for 1 hour at 4° C. The precleared supernatant was mixed with approximately 5 µg of glutathione-S-transferase or the appropriate fusion protein attached to glutathione-agarose beads for 1 hour at 4° C. The beads were collected by centrifugation and washed extensively with lysis buffer (4×500 µl) and with kinase buffer (2×500 µl: 20 mM HEPES, pH 7.4, 10 mM NaF, and 0.1% 2-mercaptoethanol). In vitro kinase assays were performed as described for 15 minutes at 37° C.

For in vitro binding and kinase assays with purified casein kinase 1 and the glutathione-S-transferase fusion proteins, a binding buffer that contained 20 mM TRIS, pH 7.6, 125 mM NaCl, 0.1% Triton X-100, 0.1% bovine serum albumin, 1 mM EDTA, and 1 mM EGTA was used. Approximately 5 µg of glutathione-S-transferase or the appropriate fusion protein attached to glutathione-agarose beads was mixed with 10 units of purified casein kinase 1 in 600 µl of binding buffer for 1 hour at 4° C. Proteins were collected by centrifugation and washed as described above (3×binding buffer and 2×kinase buffer). In vitro kinase assays were performed as described above.

Figure 8A:
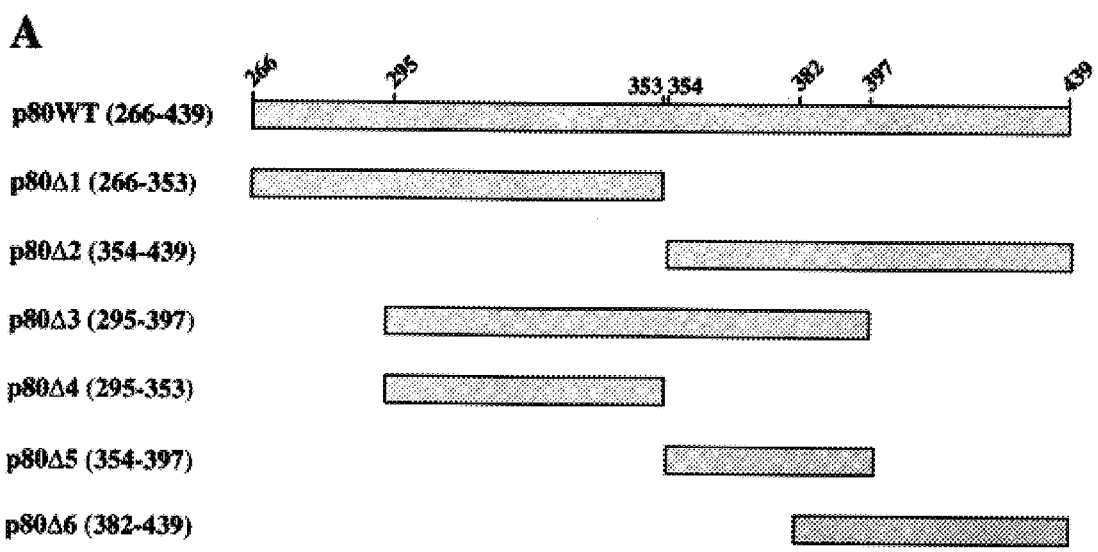
FIG. 8A shows a schematic of the cytoplasmic domain of the p80 tumor necrosis factor receptor (residues 266–439) with the deletion constructs used herein. All deletions were expressed as glutathione-S-transferase fusion proteins.
Figure 8B:
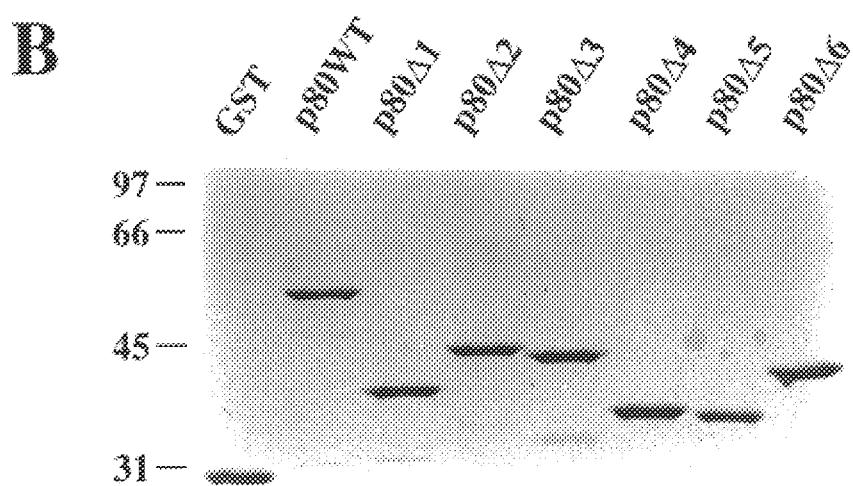
FIG. 8B shows a sodium dodecyl sulfate-polyacrylamide gel stained with Coomassie Blue of the glutathione-S-transferase fusion proteins with the indicated molecular mass standards.

The cytoplasmic domain of the p80 tumor necrosis factor receptor physically associates with a serine/threonine kinase termed p80TRAK. To define the p80TRAK binding region in the cytoplasmic domain of the p80 receptor, a series of deletions of the cytoplasmic domain were constructed as illustrated in FIG. 8A. p80 wild type (WT) contained the entire cytoplasmic domain of the p80 receptor, and p80Δ1 and p80Δ2 were the N- and C-terminal halves of the 25 cytoplasmic domain, respectively. Deletion mutant p80Δ3 had truncations at both the N- and C-terminus, and p80Δ4 and p80Δ5 were the N- and C-terminal halves of p80Δ3, respectively. The deletion mutant p80Δ6 encompassed the C-terminal 58 residues. All deletion mutants were made as glutathione-S-transferase fusion proteins, expressed in *Escherichia. coli*, and purified by affinity chromatography on glutathione agarose. A Coomassie Blue stained gel of the fusion proteins used appears in FIG. 8B.

EXAMPLE 14
p80TRAK Binds to 44 Residues of the p80 Cytoplasmic Domain

Figure 9A:
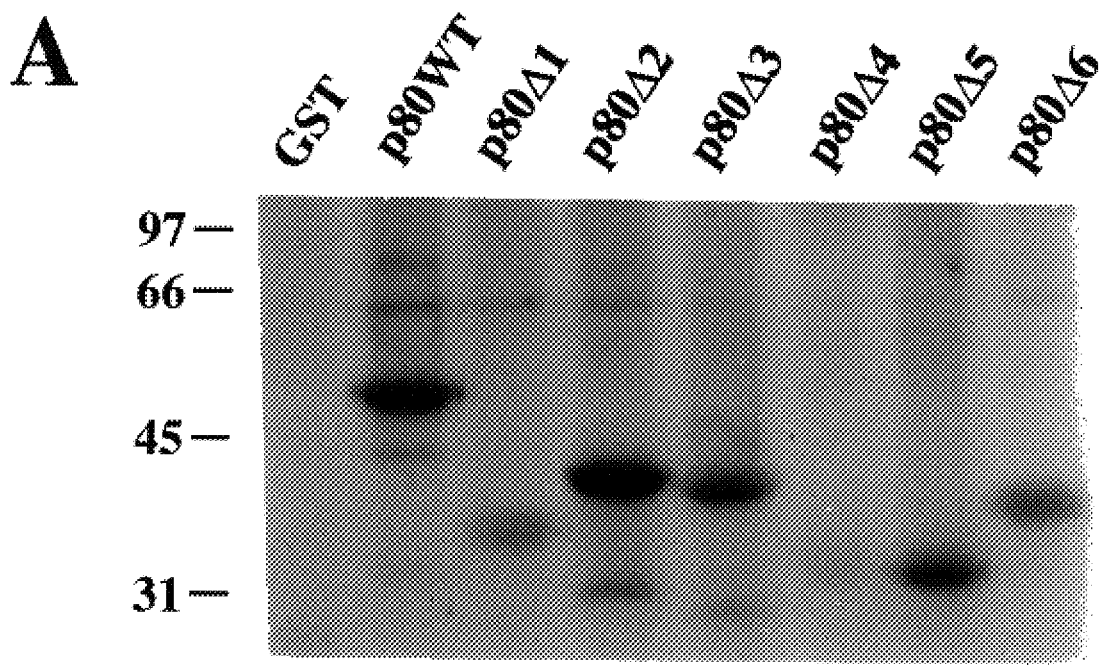
FIG. 9A shows U937 cell lysates from $2 \times 10^6$ per assay were prepared and affinity precipitations were performed with the indicated glutathione-S-transferase fusion protein. In vitro kinase assays were performed as described below. The samples were analyzed by 9% sodium dodecyl sulfate-polyacrylamide gel electrophoresis, and the dried gel exposed to X-ray film for 3 hours at −70° C. Relative mobilities for the various fusion proteins were identified by Coomassie Blue staining.

To ascertain which region of the cytoplasmic domain associates with p80TRAK, the glutathione-S-transferase fusion proteins were used in affinity precipitations of U937 cell lysates followed by in vitro kinase assays. p80TRAK activity bound to and phosphorylated p80WT, p80Δ2, p80Δ3, p80Δ5, and p80Δ6, but not glutathione-S-transferase, p80Δ1, and p80Δ4 (FIG. 9A). The phosphorylation patterns of p80WT, p80Δ1, and p80Δ2 considered together imply that the C-terminal half (p80Δ2), but not the membrane proximal half (p80Δ1) of the p80 cytoplasmic domain is necessary for p80TRAK binding. Within the C-terminal half, a small region of 44 residues (p80Δ5, residues 354–397) was sufficient for binding p80TRAK.

Figure 9B:
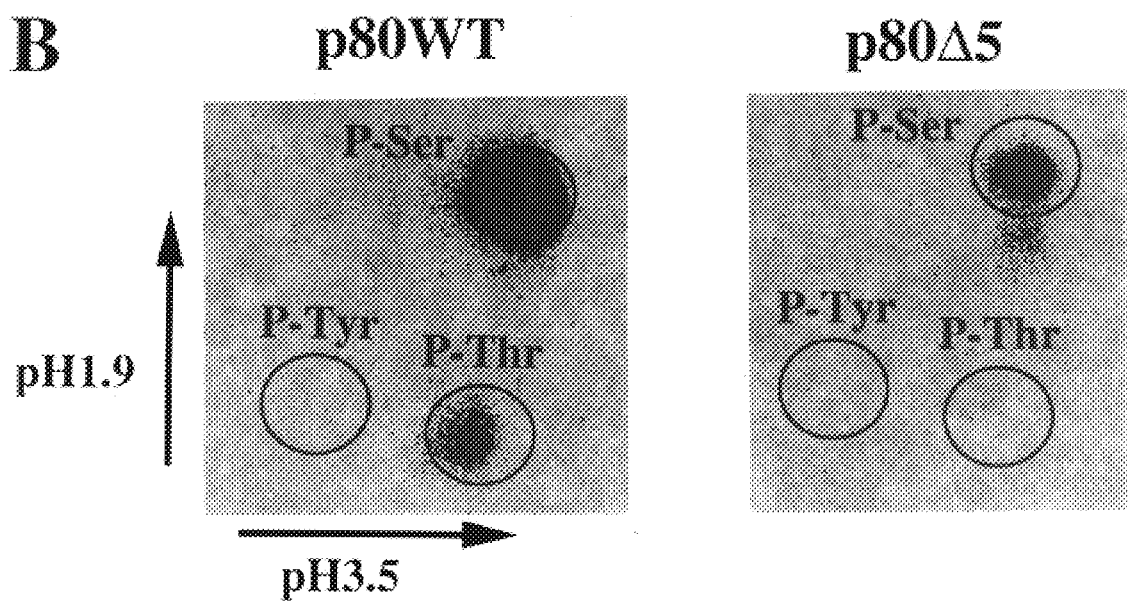
FIG. 9 shows the p80TRAK binds to and phosphorylates a minimal region of 44 residues within the p80 cytoplasmic domain.

Phosphoamino acid analysis of p80WT and p80Δ5 indicated 85% and 91% phosphorylation respectively on serine and 14% and 9% incorporation on threonine (FIG. 9B). There was no incorporation on tyrosine in either case, since the cytoplasmic domain of the p80 receptor does not contain any tyrosine residues. Thus, the minimal region of the cytoplasmic domain of the p80 receptor that interacts with p80TRAK is contained in the C-terminus, residues 354–397 (p80Δ5).

EXAMPLE 15
Purified casein kinase 1 Associates with Residues 354–397 (p80Δ5)

Figure 10A:
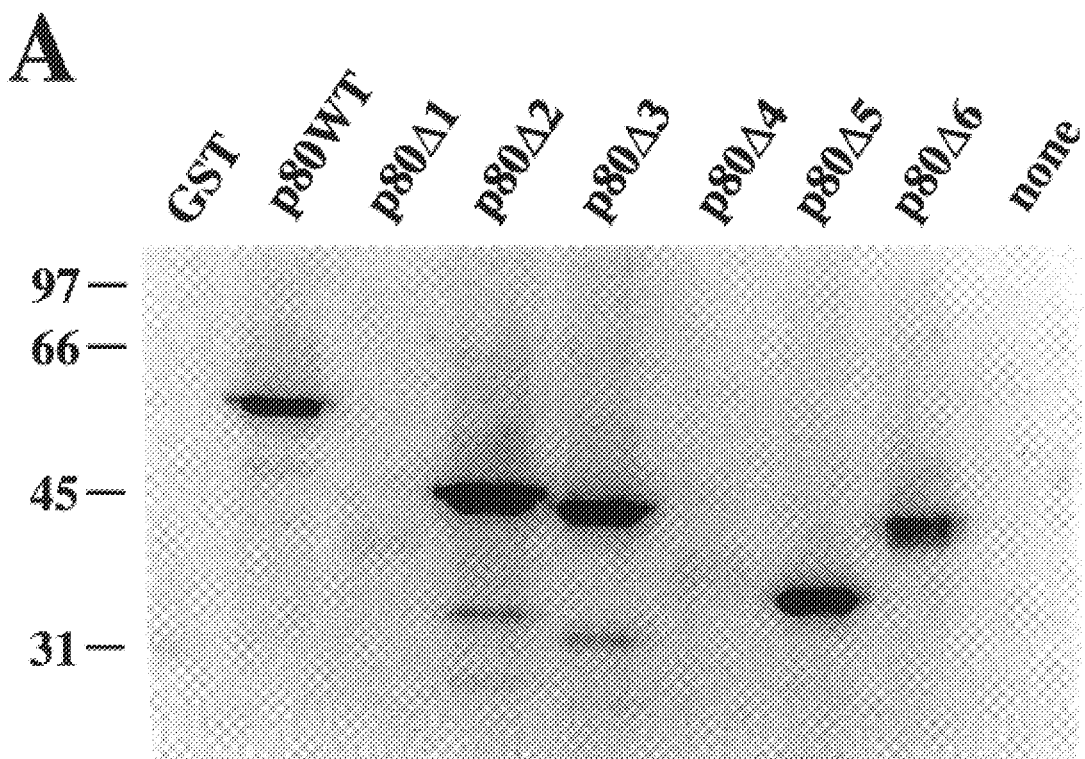
FIG. 10 shows the purified casein kinase 1 binds to and phosphorylates the p80 cytoplasmic domain. An in vitro kinase assay with 2.5 units of purified casein kinase 1 (FIG. 10A) or an in vitro binding and kinase assay with 10 units of purified casein kinase 1 (FIG. 8B) with the indicated fusion proteins was performed as described below. Reaction mixtures were analyzed by 9% sodium dodecyl sulfate-polyacrylamide gel electrophoresis, and the dried gel exposed to a PhosphorImager screen.

Immune complex kinase assays indicated coprecipitation of a serine kinase activity with the p80 tumor necrosis factor receptor from PC60 cells transfected with both tumor necrosis factor receptors. By using specific substrates and inhibitors, this kinase was identified as casein kinase 1. Since it was shown that p80Δ5 is the minimal region for binding and phosphorylation by p80TRAK and contains potential casein kinase 1 phosphorylation sites, a purified casein kinase 1 was used along with p80 deletion mutants to identify which region of the cytoplasmic domain undergoes phosphorylation. Purified casein kinase 1 phosphorylated p80WT, p80Δ2, p80Δ3, p80Δ5, and to a lesser extent p80Δ6, but not glutathione-S-transferase, p80Δ1, and p80Δ4 (FIG. 10A). Differences in the amount of phosphorylation of the glutathione-S-transferase fusion proteins by casein kinase 1 may reflect the number of different phosphorylation sites remaining in the deletion mutant. This phosphorylation pattern was similar to that for p80TRAK precipitated from U937 cell extracts (FIG. 9A).

Figure 10B:
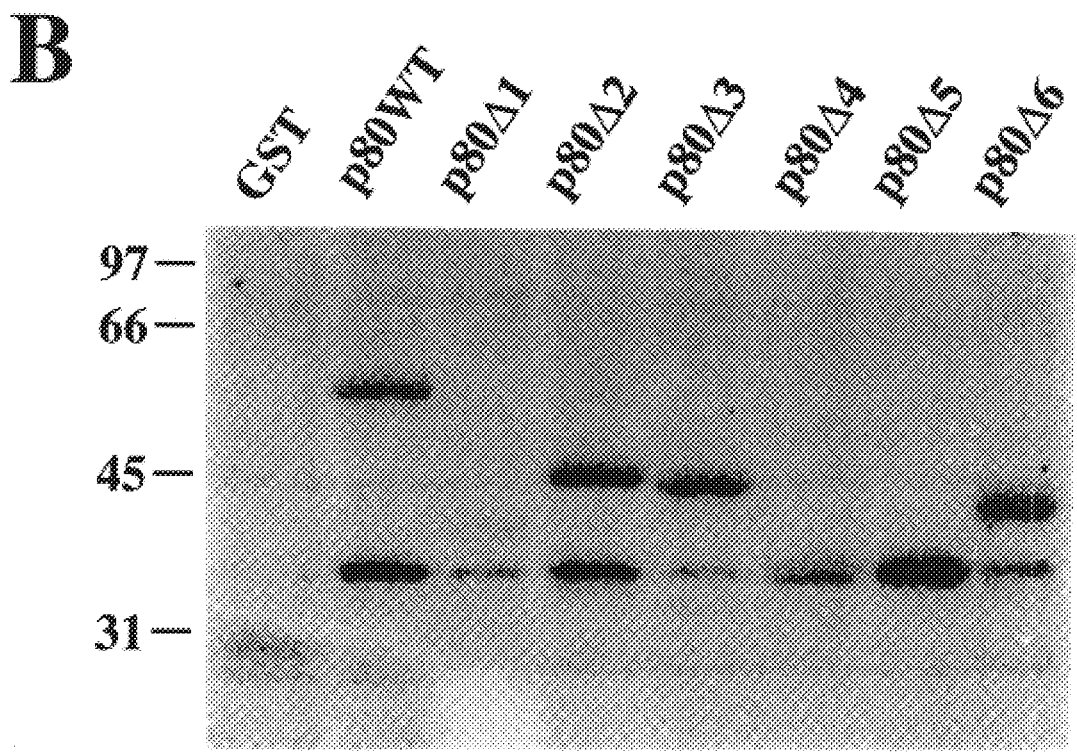

To determine whether casein kinase 1 could bind to the p80 cytoplasmic domain, purified casein kinase 1 was first incubated with each of the glutathione-S-transferase fusion proteins for 1 hour at 4° C., the mixtures were washed extensively with binding buffer, and an in vitro kinase assay was then performed (FIG. 10B). The results with purified casein kinase 1 (FIG. 10A) were indistinguishable from those obtained with p80TRAK from U937 cells (FIG. 9A). The phosphorylated band co-migrating at approximately 33 kDa may reflect phosphorylation of the purified casein kinase 1 in the presence of bovine serum albumin in the binding assay. Thus, it appears that p80TRAK activity from U937 cells precipitated with the cytoplasmic domain of the p80 receptor is related to casein kinase 1.

Figure 11A:
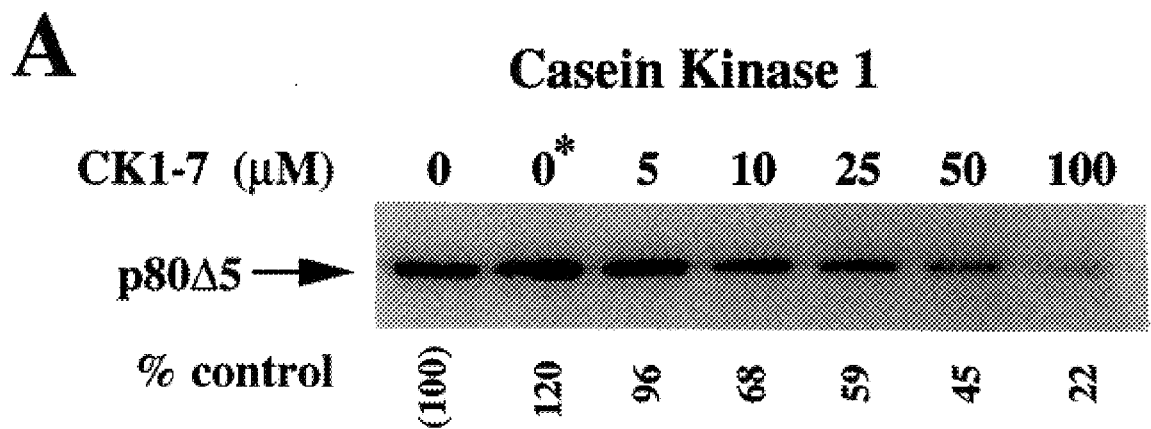
FIG. 11 shows a casein kinase 1-specific inhibitor blocks p80TRAK activity. An in vitro kinase assay with 10 units of purified casein kinase 1 (FIG. 11A) or p80TRAK precipitated from U937 cells with p80Δ5 (FIG. 8B) with p80Δ5 as a substrate was performed in the presence of the indicated concentration of casein kinase 1-7 dissolved in DMSO. The asterisk represents a control in which DMSO was added to a final concentration of 1.6%. Reaction mixtures were analyzed by 9% sodium dodecyl sulfate-polyacrylamide gel electrophoresis, and the dried gel was exposed to a PhosphorImager screen. The phosphorylation of p80Δ5 was quantitated by ImageQuant Software (Molecular Dynamics, Sunnyvale, Calif.).
Figure 11B:
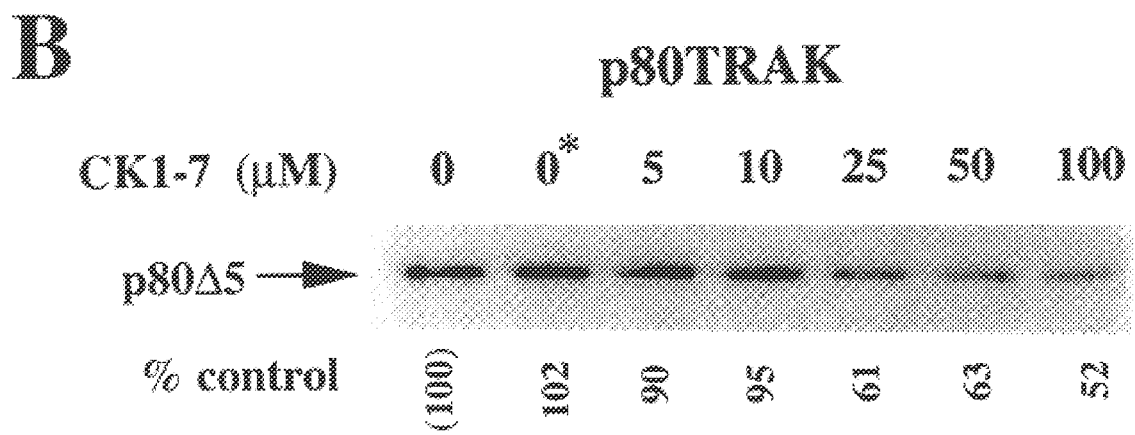

EXAMPLE 16
The casein kinase 1- Inhibitor casein kinase 1-7 Inhibits p80TRAK Activity The casein kinase 1 inhibitor casein kinase 1-7 has been reported to inhibit the phosphorylation of the p80 receptor in immune complex kinase assays and in vivo. To further support the identification of p80TRAK activity as casein kinase 1, the kinase activity of purified casein kinase 1 and p80TRAK precipitated from U937 cells with increasing concentrations of casein kinase 1-7 was compared. A concentration of 100 μM casein kinase 1-7 inhibited purified casein kinase 1 and p80TRAK by 80% and 50%, respectively, as measured by phosphorylation of p80Δ5 (FIG. 11). Thus p80TRAK activity was partially inhibited by casein kinase 1-7. That some p80TRAK activity remained active at 100 μM casein kinase 1-7 suggests that more than one kinase had been precipitated from U937 cells.

The present invention demonstrates that a minimal region of 44 residues (p80Δ5, 354–397) residing near the C-terminus of the p80 cytoplasmic domain is necessary for binding of p80TRAK and undergoes phosphorylation by p80TRAK. It was also shown using purified, recombinant casein kinase 1, that casein kinase 1's binding site and its phosphorylation of the p80 cytoplasmic domain was indistinguishable from that of p80TRAK. The phosphorylation of the p80 cytoplasmic domain by purified casein kinase 1 is in agreement with a report by Beyaert et al. Additionally, p80TRAK could be partially inhibited by a casein kinase 1-specific kinase inhibitor, suggesting that p80TRAK is similar to casein kinase 1.

The minimal region (p80Δ5; residues 354–397) of the p80 cytoplasmic domain that was serine phosphorylated by p80TRAK contains 13 serines and 4 threonine residues. Within this region, a casein kinase 1 consensus site of the sequence Ser(P)-Xaa-Xaa-Ser/Thr was repeated four times. The putative binding site of p80TRAK was also located within a region of the p80 cytoplasmic domain that is necessary for binding TRAF2 and TRAF1 factors. However, the interaction of TRAF1 with the receptor is weak and thus is indirect via its association with TRAF2. The constitutive presence of the phosphorylated form of the p80 tumor necrosis factor receptor and its association with TRAF2 may suggest that the phosphorylated form of the receptor binds to TRAF2. Whether phosphorylation of the p80 tumor necrosis factor receptor is critical for the recruitment of TRAF2 is not known.

Interestingly, blocking the phosphorylation of the p80 receptor by a casein kinase 1 inhibitor, potentiated tumor necrosis factor-induced apoptosis mediated by the p80 receptor. This result suggests an inhibitory role for phosphorylation of the receptor by casein kinase 1. Additionally, treatment of HeLa cells transfected with the p80 tumor necrosis factor receptor with a p80-specific tumor necrosis factor mutein or monoclonal antibody activated NF-κB. However, this activation could not be blocked by pretreatment with a casein kinase 1-specific kinase inhibitor, suggesting that casein kinase 1 does not play a significant role in activation of NF-κB mediated by the p80 receptor. Thus, it is likely that p80TRAK/casein kinase 1 plays a role in p80-mediated apoptosis but not p80-mediated NF-κB activation. Consequently, the overexpression of TRAF2, but not TRAF1, in human embryonic kidney 293 cells activates NF-κB in a ligand-independent manner. This observation parallels the ligand-mediated clustering of the receptor necessary for NF-κB activation.

Thus, the present invention demonstrates that a small region of approximately 44 residues of the p80 cytoplasmic domain is sufficient for binding p80TRAK and purified, recombinant casein kinase 1. The observations that the p80 tumor necrosis factor receptor is phosphorylated in vivo and that p80TRAK binds within a region also necessary for TRAF2 interaction suggests that phosphorylation of the receptor is necessary for TRAF2 association. Besides the receptor, TRAF2 itself contains potential phosphorylation sites for p80TRAK/casein kinase 1. It is possible that p80TRAK described here phosphorylates not only the receptor, but also TRAF2 and other related proteins that mediate signal transduction via the p80 tumor necrosis factor receptor.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An enriched and isolated protein kinase that associates with amino acid residues 354–397 of the cytoplasmic domain of the p80 form of the tumor necrosis factor receptor, said kinase phosphorylates both the p80 and p60 forms of the tumor necrosis factor receptor, said kinase phosphorylates a 59 kDa molecular weight protein associated with the cytoplasmic domain of the p80 form of the tumor necrosis factor receptor, and said kinase is partially inhibited by casein kinase 1-specific kinase inhibitor.

\* \* \* \* \*

UNITED STATES PATENT AND TRADEMARK OFFICE
CERTIFICATE OF CORRECTION

PATENT NO. : 5,837,817
DATED : November 17, 1998
INVENTOR(S) : Bharat B. Aggarwal and Bryant G. Darnay It is certified that error appears in the above-identified patent and that said Letters Patent is hereby corrected as shown below:

Column 2,
Line 38, "identify" should read -- identifies --.
Lines 50-51, "Tumor Necrosis Factor Receptor-II Associated Protein" should read
-- Tumor Necrosis Factor Receptor-II Associated Protein --.

Column 3,
Lines 58-60, "tumor necrosis factor receptor-associated kinase.... tumor necrosis factor receptor-associated protein" should read -- tumor nercorsis factor receptor-associated kinase...tumor necrosis factor receptor-associated protein --.

Column 8,
Line 44, "HEPES" should read -- HEPES, --.

Column 9,
Line 65, "pp59" should read -- pp59, --.

Column 10,
Line 28, "yield" should read -- yields --.
Line 31, "receptor" should read -- receptor, --.

Column 11,
Line 26, "th" should read -- the --.
Line 56, "(WT.Δ1)," should read -- (WT. Δ1) (SEQ. ID NO. 5) --.
Line 58, "(Δ 2, Δ 5)" should read -- (Δ 2, Δ 5), (SEQ. ID NO.6) --.
Line 59, "(Δ 3, Δ 4)" should read -- (Δ 3, Δ 4), (SEQ. ID NO.7) --.
Line 60, "(Δ 6)" should read -- (Δ 6), (SEQ. ID NO.8) --.
Line 62, "(SEQ. ID NO. 5) " should read -- (SEQ. ID NO. 9) --.
Line 63, "(SEQ. ID NO. 6) " should read -- (SEQ. ID NO. 10) --.
Line 65, "(SEQ. ID NO. 7) " should read -- (SEQ. ID NO. 11) --.

Column 12,
Line 2, please delete the words "(SEQ. ID NO. 10) ".
Line 3, please delete the words "(SEQ. ID NO. 11) ".
Line 52, "Escherichia. Coli." should read -- Escherichia coli --.

UNITED STATES PATENT AND TRADEMARK OFFICE
CERTIFICATE OF CORRECTION

PATENT NO. : 5,837,817
DATED : November 17, 1998
INVENTOR(S) : Bharat B. Aggarwal and Bryant G. Darnay It is certified that error appears in the above-identified patent and that said Letters Patent is hereby corrected as shown below:

<u>Column 14,</u>
Line 39, "inhibitor," should read -- inhibitor --.

Signed and Sealed this

Thirteenth Day of August, 2002

Attest:

JAMES E. ROGAN
Attesting Officer
Director of the United States Patent and Trademark Office